United States Patent [19]

Modrovich

[11] Patent Number: 4,465,770
[45] Date of Patent: * Aug. 14, 1984

[54] STABILIZED ENZYMIC SOLUTIONS FOR DETERMINING UREA

[76] Inventor: Ivan E. Modrovich, 1043 Mesa Dr., Camarillo, Calif. 93010

[*] Notice: The portion of the term of this patent subsequent to Aug. 4, 1998 has been disclaimed.

[21] Appl. No.: 287,907

[22] Filed: Jul. 29, 1981

Related U.S. Application Data

[63] Continuation of Ser. No. 074,544, Sep. 11, 1979, Pat. No. 4,282,316.

[51] Int. Cl.$^3$ .......................... C12Q 1/58; C12N 9/96
[52] U.S. Cl. ...................................... 435/12; 435/188; 435/810; 436/12; 252/408.1
[58] Field of Search .................. 435/12, 7, 188, 810; 252/408 R; 436/12

[56] References Cited

U.S. PATENT DOCUMENTS

| | | | |
|---|---|---|---|
| 3,413,198 | 11/1968 | Deutsch | 435/12 |
| 3,876,375 | 4/1975 | Marukas | 436/12 |
| 3,876,502 | 4/1975 | Monte et al. | 435/12 |
| 3,950,226 | 4/1976 | Chang | 435/12 |
| 4,169,012 | 9/1979 | Dawson et al. | 435/188 |
| 4,188,465 | 2/1980 | Schneider et al. | 435/12 |
| 4,218,535 | 8/1980 | Ray | 435/12 |
| 4,282,316 | 8/1981 | Modrovich | 435/12 |
| 4,378,430 | 3/1983 | Modrovich | 435/12 |

*Primary Examiner*—Benoit Castel
*Attorney, Agent, or Firm*—Christie, Parker & Hale

[57] ABSTRACT

A stabilized urease solution is disclosed comprising water, buffering agents, a bacteriostat, chelating agent, polyhydroxy organic compound and urease. The preferred buffering agents are selected from low conductivity Zwitterionic buffer salts, such as N-2-hydroxyethyl piperazine-N'-2-ethanesulfonic acid, triethanolamine, tris(hydroxymethyl)aminomethane, diethanolamine, aminomethyl propanol and mixtures thereof.

15 Claims, No Drawings

STABILIZED ENZYMIC SOLUTIONS FOR DETERMINING UREA

CROSS REFERENCE TO RELATED APPLICATIONS

This is a continuation of application Ser. No. 074,544, filed Sept. 11, 1979, now U.S. Pat. No. 4,282,316, and is related to application Ser. No. 215,622 filed Dec. 12, 1980, now U.S. Pat. No. 4,378,430, incorporated herein by reference.

BACKGROUND OF THE INVENTION

The present invention relates to stabilized enzymic solutions for determining urea. Such stabilized solutions have utility in determining the quantitative amount of urea in human sera, such as blood, plasma and the like. More particularly, the invention relates to stabilized enzymic solutions for use in methods for determining urea based upon conductivity measurements.

A method for determining urea was reported by W. T. Chin and W. Kroontje, "Conductivity Method for Determination of Urea," *Anal. Chem,* 33:1757–1760 (1961). The method of Chin and Kroontje was based upon the difference in electrical conductivity of urea and ammonium carbonate produced by the reaction of urease with urea in solution. The method of Chin and Kroontje was modified by P. Bourrelly and V. Bourrelly-Durand, *J. Chim. Phys.,* 62:673–677 (1965) and by M. Hanss and A. Rey, *Biochim. Biophys. Acta.,* 227:630–638 (1971).

An improvement in the method of measuring urea quantitatively using conductivity measurements was developed by G. Paulson, R. Roy and J. Sternberg, "A Rate-Sensing Approach to Urea Measurement," *Clin. Chem.,* 17:644 (1971). The improved method was based on conductivimetric rate-sensing. The method employed the rate of increase of conductivity of a solution as urease catalyzes the hydrolysis of urea to ammonium carbonate by the reaction:

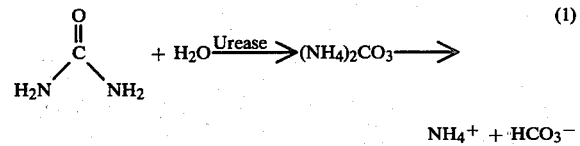

(1)

$$NH_4^+ + HCO_3^-$$

The observed rate of change of conductivity was shown to be proportional to the urea concentration in the sample. In particular, the rate of change during the interval from ten to twenty seconds following addition of the sample to a buffered urease solution at a pH 7 and temperature of 34° C. was determined to be proportional to the urea concentration. The rate-sensing method is sufficiently precise and accurate and has found routine use in clinical chemistry laboratories.

Other methods for quantitative measuring of urea are based on colorimetric and spectrophotometric analyses. For example, in the reaction sequence:

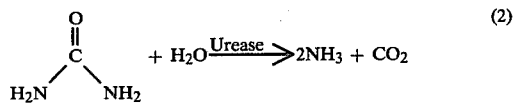

(2)

the production of ammonia or $CO_2$ can be quantitatively measured photometrically. The reaction sequence (2) above is the same as reaction sequence (1) except that (2) is written as if it were a nonaqueous system to show that ammonia and carbon dioxide are products of urease activity in urea. The ammonia produced can be measured photometrically by the reaction:

(3)

The intensity of the blue color produced can be correlated to the amount of ammonia. The ammonia can also be measured through the following reaction sequence:

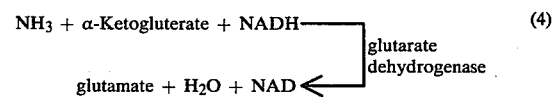

(4)

In this reaction sequence the NADH acts as a reducing agent. The NADH has an absorbance at 340 mm and the NAD does not. Thus, the absorbance at 340 mm can be correlated to the amount of $NH_3$ present in a sample.

Stability of enzymic solutions used in diagnostic assays is important in providing methods of analysis which exhibit precision and uniformity among separate determinations when conducted over a period of elapsed time. Instability of enzymic solutions, in addition to not providing reproducibility of assays, can also add to the ever increasing cost of medical services because the unstable enzymic solutions need to be discarded and fresh solutions formulated.

It has recently been estimated that about 25 percent of all in vitro diagnostic tests conducted annually in the United States, are unreliable. Unreliable tests can result in unnecessary medical treatment, the withholding of necessary treatment and lost income. Because of their high specificity, the use of enzyme determinations has significantly increased during the last few years and indications are that this trend will continue. However, rigorous quality control measures are required to assure the accuracy and consistency of results. This requirement derives from the fact that the exact nature of enzymes, as well as mechanisms of their reactions, remains unknown for the most part.

At present, the greatest limitation in the diagnostic reagent manufacture, by far, lies in the unstable characteristics of the enzymic solutions. Current urea enzymic diagnostic methodologies require the use of labile ingredients. Due to the labile nature of the enzymes, rigorous quality control is required over the production of such enzymic solutions, in the reconstituting dry media preparations and formulation of such enzymic solutions. Such quality control is costly. Moreover, if such control in any step in the process is not maintained within a high degree of control standards, the quality of the final product can be reduced materially leading to decreased precision in assay results.

The present commercial state-of-the-art technique for stabilizing the reactive ability of enzymes or coenzymes is performed by locking them into a solid matrix, either by freeze drying, dry blending such as used for tableting dry powders primarily in the pharmaceutical diagnostic and related industries, and immobilization by locking the chemical structure of the enzyme into a solid matrix. Contrary to the sophistication these terms imply, these approaches are neither practical nor desirable and are also expensive. The manufacturer is forced to remove the water and supply a partial product, thus relinquishing part of the quality control cycle in the dilution and use of the final product. Laboratories are forced to pay the high cost of packaging, reagent waste, freeze drying and dry blending. Usefulness of the product is further limited by packaging modes and sizes.

Furthermore, good product uniformity is difficult to achieve, especially in the laboratories where the products are to be utilized in diagnostic assay. This condition is exemplified by the fact that most commercial freeze-dried controlled sera (reference serum) lists the acceptable bottle-to-bottle variation of enzyme constituents at ±10 percent of the mean. Generally, the reconstituted freeze-dried urease solutions have a stability of about 24 hours to 5 days at room temperature conditions. Their use is then limited by such short shelf-life.

The present invention is uniquely designed so that the enzyme solution, although containing labile ingredients in a liquid reagent, are effectively "stabilized" thereby controlling the activity of the labile ingredients in the liquid solution. The means of stability insures long-term stability in a liquid media. Moreover, close tolerance control can be achieved in the manufacturing of a high quality product which eliminates the inconvenience of the rigid package size, the high cost of packaging and freeze drying, and reagent waste.

SUMMARY OF THE INVENTION

Labile enzymes, useful in the diagnostic assay of urea are treated according to the invention resulting in long-term stability without deleteriously affecting enzyme activity, conductimetric properties, or photometric absorptivity. The invention provides reagents wherein quality control is assured throughout manufacturing, packaging, storage, and their use. The inconvenience of rigid package size is eliminated as is the high cost of packaging, freeze drying, and reagent waste. The liquid enzyme system for urea assay, as described herein, provides desired flexibility to urea assay determination. The stabilized liquid enzyme solutions of the invention can be compared with fresh formulated reagents prepared from freeze-dried enzymes. Such studies show a one-to-one correlation between aged liquid and fresh reagents with comparable sensitivity and precision. The liquid system of the present invention offers better reagent homogeneity and packaging, as well as flexibility and usage, in contrast to the freeze-dried or dry media preparations.

In diagnostic urea assay, the stabilization of the labile components and particularly the labile urease in a ready-to-use liquid media, is a new and exciting approach to satisfy the needs of the clinical laboratory and the reliability demands of the regulatory authorities. The flexibility of these liquid systems insures their applicability to automated instrumentation, as well as their convenience in manual testings.

Stabilization of the urease useful in the determination of urea is accomplished, in accordance with the invention, by mixing tris(hydroxymethyl)aminomethane with water, which water has been treated for removal of metals and especially heavy metal ions, e.g., triple distilled water can be used. To the mixture is added N-2-hydroxyethyl-piperazine-N'-2-ethanesulfonic acid and ethylenediaminetetraacetic acid (as its disodium salt). To the mixture is added a polyhydroxy organic compound, such as glycerol, ethylene glycol, sorbitol and propylene glycol. The pH of the mixture is adjusted to about 6-8, such that the ammonia produced by the urease activity will not affect the pH. The urease is then added to the mixture.

The preferred stabilized urease solution for use in urea determination is compounded in the following manner. N-2-hydroxyethyl-1-piperazine-N'-2-ethanesulfonic acid is added and mixed in distilled water. To the mixture is added 2,4-dichlorophenol and the disodium salt of ethylenediaminetetraacetic acid. Triethanol amine is then added and the pH adjusted to the range of pH 6-8. A polyhydroxy organic compound such as glycerol, ethylene glycol, sorbitol and propylene glycol is added, and preferably glycerol is added as the polyhydroxy compound. The aqueous solution of enzyme urease is then added. The resultant solution can be used in the determination of urea. In use, the solution is diluted with water to obtain the desired amount of urease activity.

In an alternative embodiment herein of the stabilized urease solutions there can be prepared three solutions: (1) an initial solution hereafter called primary solution; (2) a reagent concentrate solution prepared from the primary solution; and (3) a diluent solution. The primary solution comprises distilled water, triethanolamine, ethylenediaminetetraacetic acid (free acid), N-2-hydroxyethyl-piperazine-N'-2-ethanesulfonic acid and 2,4-dichlorophenol. The reagent concentrate solution comprises the primary solution, a polyhydroxy organic compound such as glycerol, ethylene glycol, sorbitol and propylene glycol, and urease. The diluent solution can comprise distilled water or a solution of 2,4-dichlorophenol in distilled water, such as up to about one percent by weight 2,4-dichlorophenol and preferably 0.004 percent by weight.

The solutions herein have extended shelf life generally in useable form (diluted) of about one month at room temperature. Longer life is found at lower temperatures.

These and many other features and attendant advantages of the invention will become apparent as the invention becomes better understood by reference to the following detailed description.

DETAILED DESCRIPTION OF THE INVENTION

The stabilized enzyme solutions herein can be used in the clinical field for the determination of urea. The stabilized enzyme solutions herein can be used in conductivimetric methods of analyses or photometric analyses. The stabilized urease solutions have utility in assays based upon the following reaction sequence:

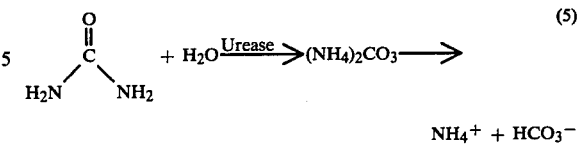

whether the conductivity, rate of change of conductivity or concentration of products (ammonia or carbon dioxide) are determined. The stabilized urease solutions herein have utility in the enzymic breakdown of urea to products which can be measured and such measurements correlated to urea concentration. In particular, the stabilized urease solutions have applicability in urea determinations based upon rate of change of conductivity. When the stabilized enzyme solutions herein are to be used in urea determinations based on photometric methods, a dye or compound absorbing light at a particular wavelength can be added to the solutions herein. For measuring urea concentration by rate of change of conductivity, the stabilized urease enzyme solutions herein can be used as described.

In the preferred utility of the stabilized urease solutions herein, the stabilized urease solutions can be used in combination with electronic analyzers which measure the conductivity, rate of change of the conductivity and correlate the measured quantities to the concentration of urea in the sample. Such instruments are commercially available and the solutions herein have especial applicability in such commercially available instruments. A particularly preferred commercially available instrument is the BUN Analyzer 2, or the "Astra ®" both available from Beckman Instruments, Inc.

Both the "Astra ®" and the BUN Analyzer 2 utilizes the enzymatic conductivimetric rate method employing a conductivity electrode immersed in the sample and an electronics system that measures the rate of increase in conductivity when a precise volume of sample is pipetted into a reaction cup containing the stabilized urease solution. When a sample is injected into the reaction cup containing the urease enzyme solution, the urea in the sample undergoes the reaction designated in reaction sequence (5) above. The reaction converts the nonionic urea to an ionic form, ammonium carbonate. During the reaction, the rate of increase of solution conductivity is directly proportional to the concentration of urea, then present in the reaction cup. The maximum observed rate measured thirteen seconds after injection of the sample has been shown to be a direct measure of the concentration of urea originally present in the sample at the time of introduction into the reaction cup. The instrument measures and holds this rate and provides a digital readout (calibrated using a standard having a known urea concentration) corresponding to the urea concentration in the sample.

The stabilized enzyme solutions herein can be prepared in a ready-to-use solution form that need only to be combined with the sample to be tested for urea content. The stabilized enzyme solutions herein can also be prepared in a concentrate form which can be diluted with a provided diluent solution or in a concentrate form which can be diluted with water by the user prior to performing a urea determination. When the stabilized enzyme solution is provided as a concentrate, it can be provided in a kit form to the end user (i.e., clinical laboratory), which kit can contain the concentrate solution and diluent solution.

The stabilized urease enzyme solution is prepared by mixing N-2-hydroxyethyl-piperazine-N'-2-ethanesulfonic acid (hereinafter referred to as HEPES) with water which has been conditioned, such as by distillation or deionization to remove metals and especially heavy metals. The water used is essentially free of such metal ions as the presence of metal ions can poison the urease enzyme. The HEPES is used in an amount that is about 0.5 to about 5 percent by weight of the water used. Amounts less than 0.5 percent by weight can be used and amounts greater than 5 percent by weight can be used, but for optimum shelf life such amounts offer no appreciable advantage. HEPES is commercially available as 4-(2-hydroxyethyl)-1-piperazineethanesulfonic acid (F.W. 238.31) from J. T. Baker Chemical Company. For the purposes herein this commercially available product can be used.

To the mixture is added a bacteriostat for enhancing the shelf life of the solution to be prepared. The bacteriostat inhibits the growth of bacteria which can be deleterious to the urease enzyme. The preferred bacteriostats inhibit bacteria growth without denaturing the urease. Alcohols can be used as the bacteriostat. The preferred bacteriostat is 2,4-dichlorophenol. The use of phenol is undesirable as it can denature the urease. The bacteriostat is added in an amount sufficient to prohibit bacterial growth. For 2,4-dichlorophenol the amount is from about 0.1 to about 1.0 percent by weight of the final solution. Lesser amounts can be used but do not offer the bacterial inhibition that is offered by 0.1 percent by weight. Amounts greater than 1.0 percent by weight can be used but offer no appreciable advantage over amounts up to 1.0 percent by weight.

To the resultant mixture is added ethylenediaminetetraacetic acid (hereinafter referred to as EDTA). The EDTA can be added as the free acid or as a salt of the acid such as the disodium salt. These forms of EDTA are commercially available and for the purposes herein the commercially available products are suitable. The EDTA is added as a chelating agent for complexing any remaining metal ions and especially heavy metal ions that can be in the solution or the sample when added. Other chelating agents can be used such as various amino acids. However, in the conductivity measuring method of urea analysis, such other chelating agents should be tested to determine their influence on conductivity and to see if they have the proper conductivity for the system. The chelating agent is added in an amount sufficient to chelate with the metal ions present, which amount is generally up to about one percent by weight.

A buffering agent such as triethanolamine is then added to the mixture. Tris(hydroxymethyl)aminomethane can also be used as a buffering compound but triethanolamine is preferred as it is less ionic and does not effect the conductivity to any substantial amount. Preferably, the buffering agent is a zwitterionic, low-conductivity buffering agent selected from the group consisting of triethanolamine, tris(hydroxymethyl)aminomethane, diethanolamine, aminomethyl propanol and mixtures thereof. HEPES can also be selected as the zwitterionic, low-conductivity buffering agent. The triethanolamine and HEPES are added to form a solution providing a pH within the range of 5-9 and preferably 6-8. The solution should contain the HEPES and triethanolamine in sufficient amounts such that the produced ammonia by the reaction of urease or urea does not effectively change the pH of the media. The pH is preferably on the low side of 7 to permit optimum enzyme activity. At a pH greater than 9 and even greater than 8, some ammonia produced by the reaction of urease and urea can be freely liberated from the solution.

A polyhydroxy organic compound is then added to the mixture for aiding the stabilization of the urease enzyme. Preferred polyhydroxy organic compounds can be selected from the group consisting of glycerol, ethylene glycol, sorbitol, and propylene glycol. The preferred polyhydroxy compound is glycerol. Generally, the polyhydroxy compound is used in an amount of about 50 percent by volume of the solution.

The urease enzyme is then added to the solution. The urease enzyme comes from the Jack Bean and is commercially available in a freeze-dried form, concentrated salt or glycerol suspension. All of these forms can be used, however, if conductivimetric analyses are to be used, the salt form is undesirable as it can affect conductivity. The urease is added in a amount which provides about 25,000 IU/l±25 percent in the working solution, that is, the solution that is combined with the sample to be tested. Appropriately, the amount of urease added to a stabilizing solution depends on whether the solution is to be a working solution or a concentrate solution. The activity of the urease is in terms of the GLDH method wherein one IU of enzyme activity in an ADP activated assay system determined at 37° C. and pH 7.5 is that amount of urease that consumes 1 mM of urea per minute under the assay conditions. As a general rule of thumb, 1 unit per Nessler analysis is equivalent to 3 units by the GLDH method.

The stabilized urease solution, when formed as a concentrate, has a projected shelf life of greater than two years at 4° C. The combined, or diluted, stabilized urease solution has a stability of four to six weeks at room temperature which correlates to about six months at 4° C.

The stabilized urease solution can be provided in a concentrate form by combining water, triethanolamine, EDTA, HEPES, 2,4-dichlorophenol, glycerol and urease in a relatively high amount such that the concentrate solution can be appropriately diluted to provide the desired 25,000 IU/l±25 percent. A diluent can be water (essentially metal and heavy metal free) which can be added by the user or can be a provided diluent. The provided diluent can be a 0.004 percent by weight aqueous solution of 2,4-dichlorophenol. This diluent and enzyme concentrate can be provided in kit form to the clinical laboratory for dilution prior to using.

The stabilized urease solutions are further illustrated by, but not intended to be limited to, the following examples.

EXAMPLE 1

A stabilized urease solution for use in the rate of change of conductivity method of urea analysis was prepared by mixing 2.07 grams (g) HEPES in 240 ml distilled water. To the mixture was added 2.5 g 2,4-dichlorophenol and 1.4 g disodium salt of EDTA. The mixture was thoroughly mixed and 0.9 ml of triethanolamine was added. The pH of the solution was measured and found to be pH 6.97.

Glycerol, in an amount of 250 ml was added. The urease enzyme from Jack Bean source, having an activity of 122 U/mg was added in an amount of 1.0 g which was dissolved in 10 ml of water prior to additions. The mixture was thoroughly mixed to dissolve the materials.

The resultant solution provided an enzyme concentrate solution which was diluted in the ratio of one part enzyme concentrate solution to nine parts water. The diluted solution had a pH 7.03 and was useful in the determination of urea in a sample when used in a Beckman BUN Analyzer 2 and "Astra ®".

The enzyme concentrate solution and the diluted solutions formed therefrom exhibited good stability.

EXAMPLE 2

The procedure of Example 1 was repeated in every essential detail except the components were combined in the following amounts:
  500 ml: Distilled H$_2$O
  4.14 g: HEPES
  1.0 g: 2,4-Dichlorophenol
  2.8 g: Na$_2$EDTA
  1.88 ml: Triethanolamine which provided a pH 7.0±0.05. To this solution was added 500 ml glycerol and 250 KU urease (salt free).

The resultant solution was a stabilized urease concentrate solution which was diluted in a 1:9 ratio with water to provide a diluted stabilized urease solution which had utility in the BUN Analyzer 2 for determining urea in a sample.

In a first diluted solution (1:9 with water), the solution had a measured conductivity of 36 which corresponded to a 47 for a 2 mM NaCl solution on the analyzer's linear scale. This diluted solution provides a standard solution which can be used in setting the scale of the BUN Analyzer 2.

In a second diluted solution (1:9 with water), the solution had a measured conductivity of 38 when measured as above. This diluted solution also had utility as a standard solution in calibrating the BUN Analyzer 2.

The concentrate and diluted solutions exhibited extended shelf-lives.

EXAMPLE 3

A primary solution was prepared by mixing 0.45 liters of triethanolamine in 0.91 liters of distilled water. To the mixture was added 0.02922 Kg of EDTA (free acid) and dissolved. There was then added 0.04766 Kg of HEPES and 0.001 Kg 2,4-dichlorophenol. The resultant primary solution was filtered through a glass fiber filter to remove any gross undissolved particles.

A stabilized reagent concentrate solution was prepared by mixing 0.1 liters of the above prepared primary solution and 0.505 liters of glycerol. Into the mixture was sprinkled 250 KIU urease which was allowed to dissolve into the mixture by diffusion at 2°–8° C. When the urease had dissolved, the resultant solution was gently mixed for about one hour to obtain a homogeneous solution.

The resulting stabilized reagent concentrate solution is diluted in a ratio of one part concentrate to 10 parts water to obtain the working or useable stabilized urease enzyme solution for use in the Beckman BUN Analyzer 2.

EXAMPLE 4

The procedure of Example 3 was repeated in every essential detail except the formed stabilized reagent concentrate solution was diluted with a diluent which was 0.004 percent by weight 2,4-dichlorophenol. The 0.004 percent diluent solution was prepared by adding 50 ml of 0.4 percent by weight aqueous 2,4-dichlorophenol solution to 1.765 liters of distilled water.

The diluent solution is then combined with 200 ml of the stabilized enzyme concentrate solution to provide a diluted stabilized urease enzyme solution which can be used for urea analysis in the Beckman BUN Analyzer 2.

The resultant diluted stabilized urease solution was stable for one month at room temperature.

EXAMPLE 5

The procedure of Example 1 was repeated in every essential detail with the exception that the stabilized urease concentrate solution had the following composition:
  HEPES: 18 mM±5%
  EDTA: ~10 mM
  Urease: 250,000 IU/l±5%

The above concentrate solution was diluted by mixing 1 ml of the concentrate with 9 ml of deionized water. The diluted stabilized urease solution had the following composition:

HEPES: 1.8 mM
EDTA: ~1 mM
Urease: 25,000 IU/l

The diluted stabilized urease solution was a clear, clean solution having a pH 7.10±0.2 at 25° C. The solution had a linearity of 2 percent at 50 mg/dl and 5 percent at 100 mg/dl (IML diluted reagent +10 microliter sample). The dynamic range for the diluted solution was 100 mg/dl. The concentrated stabilized urease solution had a stability of 72 hours at 41° C. The diluted stabilized urease solution exhibited a stability of four weeks at room temperature and four months under refrigeration (~4°–8° C.).

EXAMPLE 6

A stabilized urease solution was prepared by mixing 50.6 ml triple distilled water and 61 mg tris(hydroxymethyl)aminomethane. To the mixture was added 70 mg HEPES with mixing. To this mixture was added 100 mg Na$_2$EDTA. Anhydrous glycerol was added in an amount of 50.6 ml and the mixture mixed for about one hour.

The PH was adjusted by adding HEPES to 7.60±0.02.

To the solution was added 75,000 IU/l urease which was added in the manner described in Example 3. The urease had an activity of 58,424 IU/g. The amount of urease was 128 mg. Diffusion took about two to three hours and the resultant solution was thoroughly mixed after dissolution with gentle stirring for about two to three hours.

EXAMPLE 7

The procedure of Example 6 was repeated in every essential detail except the components were present in the following amounts:

Tripled Distilled H$_2$O: 200 ml
Tris(hydroxymethyl)aminomethane: 0.244 g
HEPES: 0.350 g
EDTA: 0.500 g
Glycerol (anhydrous): 200 ml
Urease: 0.640 g It has been found that the stabilized enzyme solutions herein have and retain sufficient activity to provide good precision and assay of urea when formulated by the method described herein.

What is claimed is:

1. A stabilized urease solution comprising essentially heavy metal ion-free water, urease enzyme present in an amount of about 25,000 IU/l±25 percent, a low-conductivity zwitterionic buffering agent present in an amount sufficient to maintain pH in the range of from about 5 to 9, a bacteriostat which is nondenaturing with respect to urease and present in an amount sufficient to inhibit bacteria growth, a chelating agent in an amount sufficient for complexing heavy metal ions, and a polyhydroxy organic compound present in an amount sufficient to stabilize the urease enzyme.

2. A stabilized urease solution as recited in claim 1 wherein the buffering agent is N-2-hydroxyethyl-piperazine-N'-2-ethanesulfonic acid in an amount of about 0.5 to about 5 percent by weight of the water.

3. A stabilized urease solution as recited in claim 1 wherein the water is essentially heavy metal-free.

4. A stabilized urease solution as recited in claim 1 wherein the bacteriostat is 2,4-dichlorophenol.

5. A stabilized urease solution as recited in claim 1 or 4 wherein the bacteriostat is present in an amount from about 0.1 to about 1.0 percent by weight.

6. A stabilized urease solution as recited in claim 1 wherein the chelating agent is ethylenediaminetetraacetic acid.

7. A stabilized urease solution as recited in claim 1 wherein the buffering agent is triethanolamine.

8. A stabilized urease solution as recited in claim 1 wherein the pH is in the range of about 6 to 8.

9. A stabilized urease solution as recited in claim 1 wherein the polyhydroxy organic compound is selected from the group consisting of glycerol, ethylene glycol, sorbitol, and propylene glycol.

10. A stabilized urease solution as recited in claim 1 wherein the polyhydroxy organic compound is present in an amount of about 50 percent by volume.

11. A stabilized urease solution as recited in claim 1 wherein the urease is present in an amount greater than 25,000 IU/l.

12. A stabilized urease solution as recited in claim 1 wherein the urease is present in an amount of about 25,000 IU/l.

13. A stabilized urease solution as recited in claim 1 wherein the zwitterionic, low-conductivity buffering agent is selected from the group consisting of N-2-hydroxyethyl-piperazine-N'-2-ethanesulfonic acid, triethanolamine, tris(hydroxymethyl)aminomethane, diethanolamine, aminomethyl propanol, and mixtures thereof.

14. A kit comprising a stabilized concentrated urease solution comprising urease enzyme, essentially heavy metal ion-free water, N-2-hydroxyethyl-piperazine-N'-2-ethanesulfonic acid present in an amount sufficient to provide on dilution a pH of from about 5 to 9, 2,4-dichlorophenol, ethylenediaminetetraacetic acid present in an amount sufficient to chelate heavy metal ions present in the solution, triethanolamine, and a polyhydroxy organic compound selected from the group consisting of glycerol, ethylene glycol, sorbitol, and propylene glycol present in an amount sufficient to stabilize the urease enzyme, the urease enzyme being present in an amount greater than 25,000 IU/l±25%.

15. A kit as recited in claim 14 further comprising a diluent solution selected from water and a 0.004 percent by weight aqueous solution of 2,4-dichlorophenol for combining with the stabilized concentrated urease solution to form a stabilized diluted urease solution having a urease enzyme activity of about 25,000 IU/l±25%.

* * * * *